United States Patent [19]

Al-Ghatta

[11] Patent Number: 5,073,203

[45] Date of Patent: Dec. 17, 1991

[54] METHOD FOR RECYCLING POLYETHYLENE TEREPHTHALATE (PET) BEVERAGE BOTTLES BY TREATING WITH CARBON DIOXIDE

[75] Inventor: Hussain A. Al-Ghatta, Fiuggi, Italy

[73] Assignee: Cobarr SpA, Anagni, Italy

[21] Appl. No.: 607,184

[22] Filed: Oct. 31, 1990

[30] Foreign Application Priority Data

Nov. 8, 1989 [IT] Italy .................. 67980 A89

[51] Int. Cl.$^5$ .................................. B08B 5/00
[52] U.S. Cl. ........................ 134/11; 134/30; 134/42; 422/33
[58] Field of Search ............... 134/11, 17, 21, 30, 134/42; 422/33

[56] References Cited

U.S. PATENT DOCUMENTS

| 2,069,820 | 2/1937 | Dodge | 422/33 |
| 4,361,536 | 11/1982 | Leopardi | 422/33 |
| 4,543,364 | 9/1985 | Nankee et al. | 528/491 |

Primary Examiner—Theodore Morris
Assistant Examiner—Saeed Chaudhry
Attorney, Agent, or Firm—Sughrue, Mion, Zinn, Macpeak & Seas

[57] ABSTRACT

A method for recycling polyethyleneterephthalate beverage bottles comprises the removal of the contaminants with the use of supercritical carbon dioxide. The recycled material is placed in an autoclave and treated with carbon dioxide at a temperature greater than 31° C. and a pressure greater than 50 bars.

2 Claims, 3 Drawing Sheets

CHROMATOGRAM 3.1
*SPECIFIC SIGNAL OF DDT*

CHROMATOGRAM 3.2
*SPECIFIC SIGNAL OF METHOXYCHLOR*

CHROMATOGRAM 3.3
*SPECIFIC SIGNAL OF NEOPYNAMIN*

METHOD FOR RECYCLING POLYETHYLENE TEREPHTHALATE (PET) BEVERAGE BOTTLES BY TREATING WITH CARBON DIOXIDE

BACKGROUND OF THE INVENTION

The present invention relates to a method for recycling polymer materials based on polyethyleneterephthalate (PET) and polyethyleneterephthalate copolymers, particularly for recycling polyethyleneterephthalate food packagings such as beverage bottles.

The general known method comprises the step of chopping the bottles into small pieces and of separating the PET material from aluminium cap, adhesively bounded paper and polyethylene foot or cup using float-sink techniques or air separation.

Until now, the food-grade resins and particularly the PET resins are not suitable for reuse as beverage containers because of possible contamination which could interfere with blow molding or with cleanliness required for a food package. Such contamination may derive from an improper use of the bottles in the household to contain liquids (aceton, acetic acid etc.) which diffuse in the bottle walls.

SUMMARY OF THE INVENTION

The object of the present invention is to provide a method for recycling PET resins which makes them adapted to be reused for food applications.

According to the invention, this object is achieved by virtue of the fact that the materials are treated in an atmosphere containing carbon dioxide under supercritical conditions.

When recycled PET resins, for instance in the forms of crushed bottles, are submitted to a supercritical fluid extraction using an atmosphere containing carbon dioxide, the supercritical fluid penetrates the surface of the crushed bottles and extracts the contaminants and impurities out of it.

A mixture of supercritical $CO_2$ and other supercritical fluids, especially water vapor, could be also used for the purification of the recycled PET.

In order to obtain the best results in the extraction of the impurities, pressures greater than 50 bars and temperatures between 31° and 245° C. are preferred.

The invention would be better understood with the aid of the following examples, whose contents should not be understood as limiting of the scope of the present invention.

DETAILED DESCRIPTION OF THE INVENTION

Figure 1:
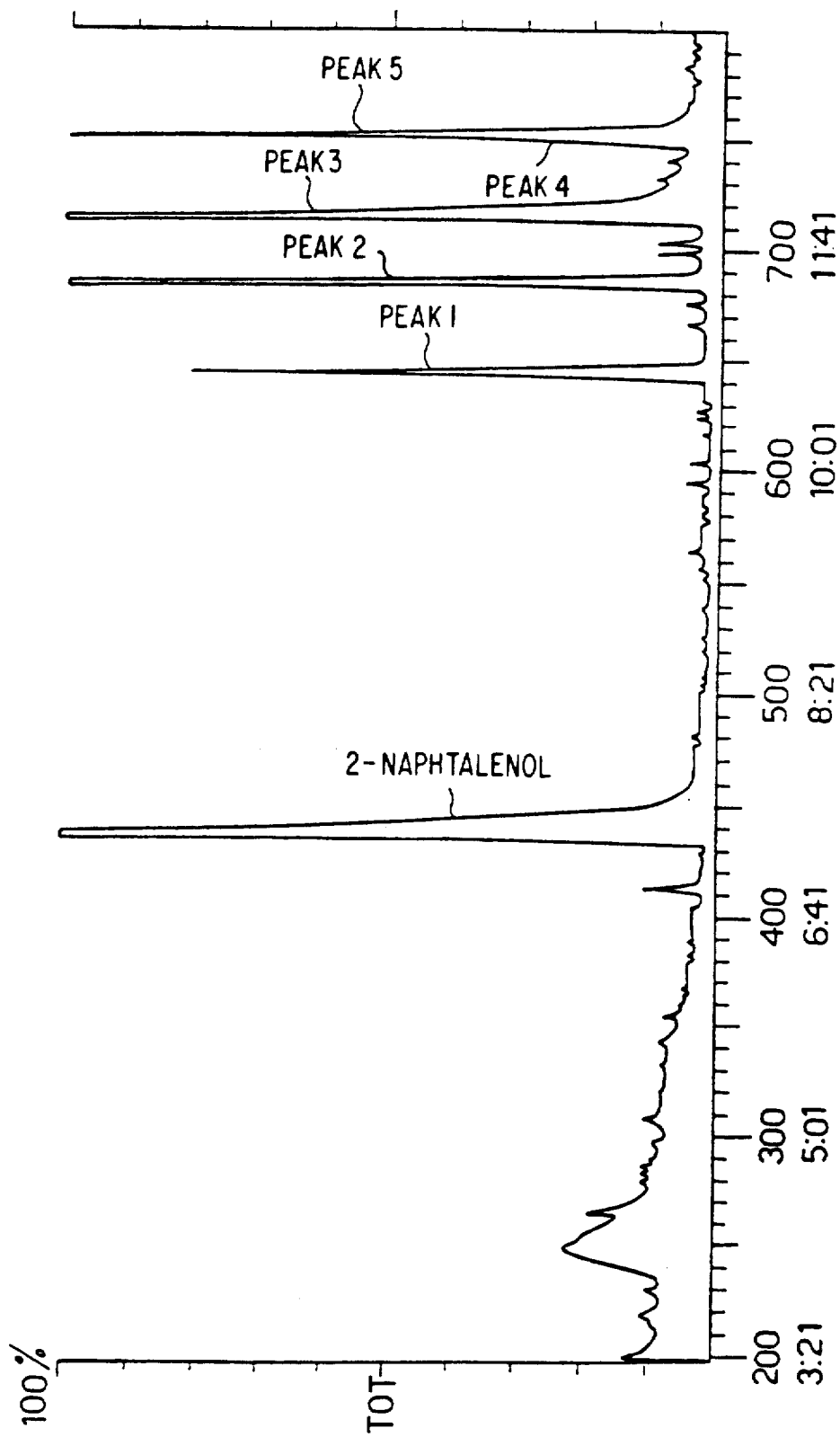
FIGS. 1-5 are chromatograms obtained in conjunction with Example 7.

The impurities contents of the examples have been measured by the head space gas chromatographic (G. C.) method described in EP-A-86830340.5.

EXAMPLE 1

20 kg of recycled PET crushed bottles, contaminated with aceton to a level of 10.500 ppm, were treated in an autoclave containing $CO_2$ and 2% by weight of water vapour at 100 bars for 3 hours at an average temperature of 120° C. The gas chromatograph test of the powdered PET after the treatment shows no aceton. The intrinsic viscosity of PET crushed bottles before and after the treatment was respectively 0,787 and 0,778 dl/g.

EXAMPLE 2

20 kg of recycled PET, contaminated with acetic acid to a level of 20100 ppm, were treated in an autoclave containing $CO_2$ at 250 bars for 2 hours at an average temperature of 130° C.

The gas chromatographic test shows a content of 3 ppm of acetic acid. There is no decrease in the intrinsic viscosity of the polymer before and after the treatment.

EXAMPLE 3

20 kg of recycled PET, contaminated with carbon tetrachloride to a level of 10250 ppm, were treated in an autoclave containing $CO_2$ at 280 bars for 5 hours at an average temperature of 150° C.

The gas chromatographic test of the powdered PET after the treatment shows no carbon tetrachloride.

There is no decrease in the intrinsic viscosity.

EXAMPLE 4

200 kg of recycled PET, contaminated with trichlorethane to a level of 500 ppm, were treated in an autoclave containing $CO_2$ at 150 bars for 3 hours at an average temperature of 145° C. The G.C. test shows a content of 2,3 ppm of trichlorethane. There is no decrease of intrinsic viscosity.

EXAMPLE 5

200 kg of recycled PET, contaminated with methylbenzoate to a level of 220 ppm, were treated in an autoclave containing $CO_2$ at 165 bars for 5 hours at an average temperature of 155° C.

The G.C. test shows a content of 1,2 ppm of methylbenzoate. There is no decrease of intrinsic viscosity.

Other tests were carried out filling PET bottles with fungicides, insecticides, deodorants, naphta and leaving them on a shalf for one week.

Then the bottles were emptied, crushed and treated according to the present invention. From the recycled PET, new bottles were obtained. These new PET bottles were filled with water that, after a storage of 3 months in the bottles at 40° C. has shown no appreciable taste, and it was not possible to detect any of the above impurities in the water.

EXAMPLE 6

Recycled PET polluted with the products identified in the following table were treated in autoclave containing humified $CO_2$ (0,5% $H_2O$) at 130 bars for three hours at an average temperature of 80° C. The test was repeated for each class of pollutant.

For the analysis of the samples, after and before the treatment with $CO_2$, the polluted PET has been extracted for 24 hours with n-hexane. The effectiveness of the supercritical $CO_2$ treatment has been determined by gas chromatographic mass spectrometer analysis of the extraction solution. A Perkin Elmer Gas Chromatograph series 8420 with capillary column length 12 m and internal diameter 0,2 mm (phase OV1—Ion Trap Detector—Mass Spectrometer) coupled with NBS/EPA Library of 42.000 Mass Spectra has been used. The results are shown in the following table.

| Test No. | Group Contaminants | Contaminant | Amount prior to treatment (ppm) | Amount subsequent to treatment (ppm) |
|---|---|---|---|---|
| 6.1 | A | CAPTAN | 5 | None detected |
|  |  | DINOCAP | 5 | None detected |
|  | FUNGICIDE | VINCLOZOLIN | 151 |  |
| 6.2 | B | BENDIOCARB | 13 | None detected |
|  | INSECTICIDE | MALATHION | 1 | None detected |
| 6.3 | C | BENTAZON | 139 | None detected |
|  | HERBICIDE | METRIBUZIN | 5 | None detected |
| 6.4 | F DRY CLEAN FLUID | ETHYLENE TRICHLORO | 19.4 | None detected |

EXAMPLE 7

Recycled PET polluted with household insecticide (type COMBO commercialized by BASF AGRITALIA S.p.A.) were treated in autoclave containing $CO_2$ at 100 bars for four hours. For the analysis of the sample the same instrumentation of example 6 has been used. Only a qualitative analysis by NBS/EPA Library has been obtained, on which are based the identifications of all the peaks displayed in chromatogram 1 shown in FIG. 1. The peaks are due to the presence of several compounds which have been identified as the following normal home-insecticide content:

Peak 1: DDT PP' 1,1 BIS (4 CHLOROPHENYL) -2,2,2-TRICHLOROETHANE
Peak 2: DDT 1,1 BIS (4 CHLOROPHENYL) -2,2,2-TRICHLOROETHANE
Peak 3: P.B.O. PHENOL, 4 (5,6,7,8 TETRAHYDRO-1,3-DIOXOLO (4,5,6) ISOQUINOLIN-S-YL) HET
Peak 4: NEOPYNAMIN
Peak 5: METOXYCHLOR (2,2-BIS (4-METHOXYPHENYL)-1,1,1-TRICHLOROETHANE)

Figure 2:
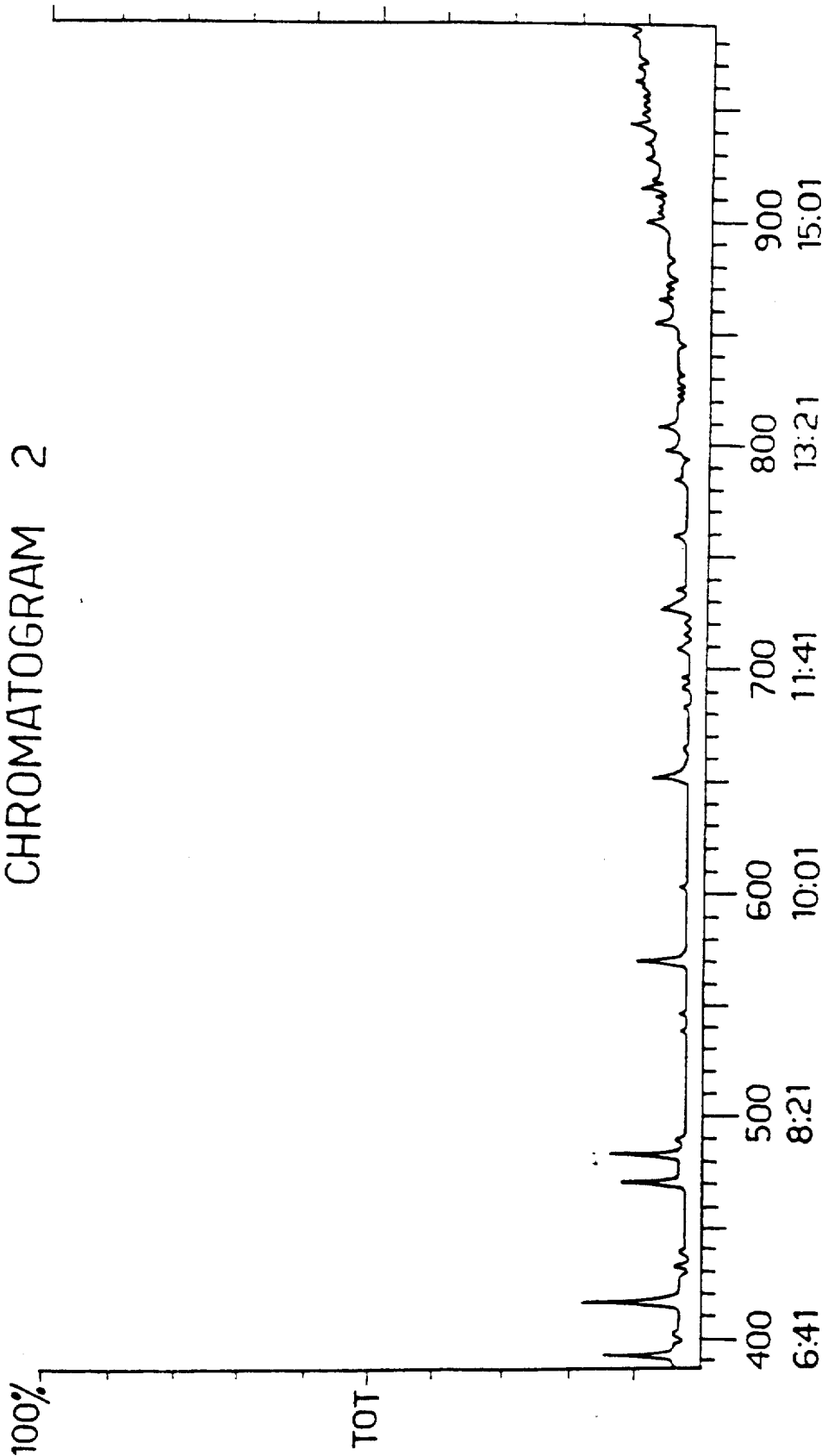
Figure 3:
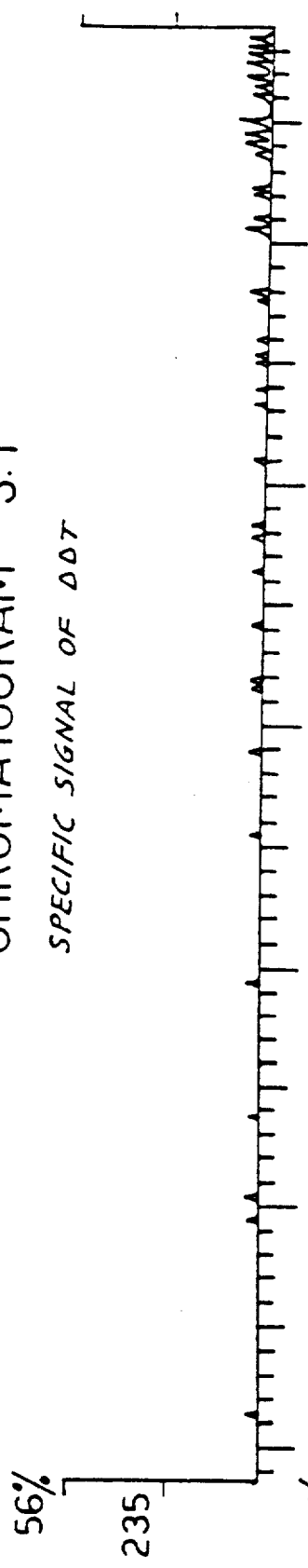
Figure 4:
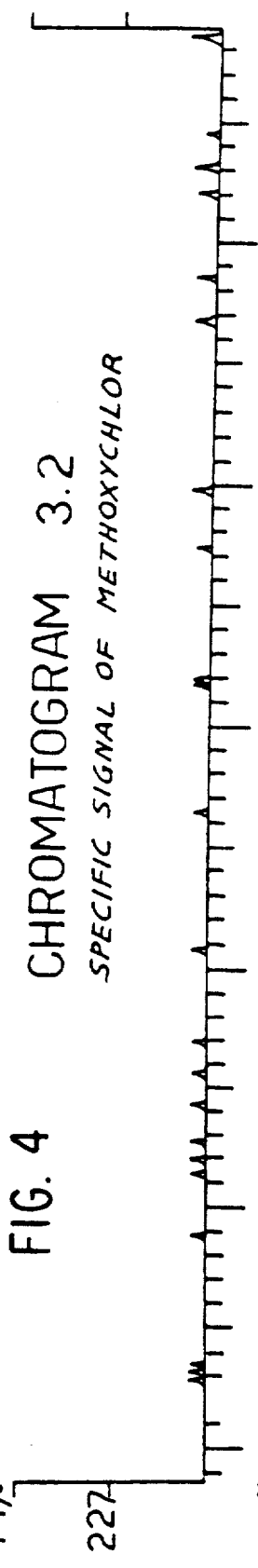
Figure 5:
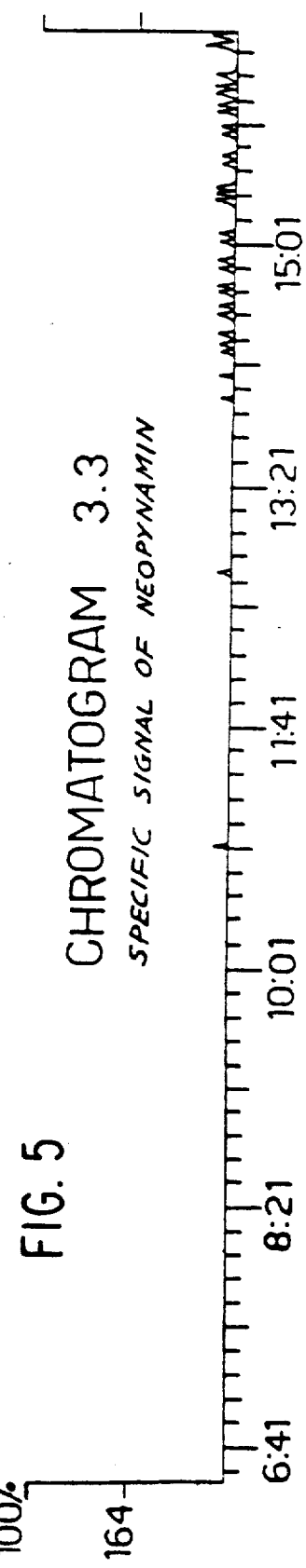

The sample treated with supercritical $CO_2$ shows the chromatogram 2 shown in FIG. 2. No signal from pesticides is detectable using a higher sensitive monitoring (chromatograms 3.1, 3.2, 3.3 shown in FIG. 3-5 instead of the general purpose investigation technique used for the chromatograms 1 and 2.

I claim:

1. A method for recycling food packagings made of polymer materials, particularly for recycling polyethyleneterephthalate beverage bottles, comprising:
   introducing contaminated recycled polyethyleneterephthalate material into an autoclave; and
   treating said polyethyleneterephthalate material in said autoclave in an atmosphere containing carbon dioxide at a pressure greater than 50 bars and a temperature greater than 31° C.

2. A method as set forth in claim 1, further comprising introducing water vapor into said autoclave in addition to said carbon dioxide.

* * * * *